United States Patent [19]

Van der Knaap

[11] Patent Number: Plant 6,433

[45] Date of Patent: Nov. 29, 1988

[54] CHRYSANTHEMUM PLANT NAMED SALMON BIJOUX

[75] Inventor: Jacques C. M. Van der Knaap, De Lier, Netherlands

[73] Assignee: Fides Research and Breeding B.V., De Lier, Netherlands

[21] Appl. No.: 915,107

[22] Filed: Oct. 3, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Salmon Bijoux particularly characterized by its lavender pink tubular ray floret color; green (immature) to yellow (mature) disc floret color; nine week response; spider/anemone capitulum form, and by its excellent flower production.

1 Drawing Sheet

The present invention comprises a new and distinct cultivar of Chrysanthemum, botanically known as *Chrysanthemum morifolium*, Ramat., and referred to by the cultivar name Salmon Bijoux.

Salmon Bijoux was discovered by applicant in 1983 as a spontaneous mutation of Bijoux, a cultivar of applicant disclosed in a pending application.

Salmon Bijoux was the result of an induced radiation program conducted by applicant in De Lier, The Netherlands, in 1983. Plants of the parent cultivar Bijoux were subjected to radiation levels of 1750 rad X-rays. Salmon Bijoux was discovered and selected as a mutation by virtue of its lavender pink ray floret color, and by its green (immature) to yellow (mature) disc floret color. The ray floret color of Bijoux is more lavender, and the disc floret color of Bijoux is green (immature) to purple-red (74D).

The first act of asexual reproduction of Salmon Bijoux was accomplished when vegetative cuttings were taken from the initial selection in August 1983 in a controlled environment in De Lier, The Netherlands by a technician working under formulations established and supervised by Jacques C. M. Van der Knaap. Horticultural examination of selected units initiated in 1983 has demonstrated that the combination of characteristics as herein disclosed for Salmon Bijoux are firmly fixed and are retained through successive generations of asexual reproduction.

Salmon Bijoux has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Salmon Bijoux which, in combination, distinguish this Chrysanthemum as a new and distinct cultivar:

1. Spider/anemone capitulum form.
2. Lavender pink tubular ray floret color.
3. Medium green (immature) to yellow (mature) disc florets.
4. Nine week response.
5. Excellent flower production per stem.
6. 60 mm diameter across face of capitulum.

7. The center cushion of Salmon Bijoux (as well as its parent Bijoux) is relatively raised to provide a unique appearance, with the outer row of mature disc florets forming petaloids which in time form the tubes. The color of the petaloids is intermediate the color of the mature disc florets and tubes, varying considerably depending on the maturity of the flower.

The accompanying photographic drawing shows typical inflorescence and foliage characteristics of Salomon Bijoux, with colors being as accurate as possible with photographs of this type.

In the following description, color references are made to The Royal Horticultural Society Colour Chart. The color values were determined in August 1986 under natural daylight at De Lier, The Netherlands.

Classification:

*Botanical.*—*Chrysanthemum morifolium*, Ramat., cv. Salmon Bijoux.

*Commercial.*—Spider/anemone spray.

INFLORESCENCE

A. Capitulum:
- *Form.*—Flat.
- *Type.*—Spider/anemone.
- *Diameter across face.*—60 mm.

B. Corolla of ray florets:
- *Color (general tonality from a distance of three meters).*—Lavender-pink with green-yellow disc floret center.
- *Color (tube and upper surface of spoon).*—36C–D.
- *Color (under surface).*—Slightly lighter than 36C–D.

C. Corolla of disc florets:
- *Color (mature).*—7C.
- *Color (immature).*—144D.

D. Reproductive organs:
- *Androecium.*—Only rudimentary in disc florets.
- *Gynoecium.*—Present in both ray and disc florets.

PLANT

A. General appearance:
- *Height.*—80 cm.

B. Foliage:
- *Color (upper surface).*—147B.
- *Color (under surface).*—147A.
- *Shape.*—Medium to long, lobed and finely serrated.

I claim:

1. A new and distinct Chrysanthemum plant named Salmon Bijoux, as described and illustrated, and particularly characterized by its lavender pink tubular ray floret color; green (immature) to yellow (mature) disc floret color; nine week response; spider/anemone capitulum form, and excellent flower production.

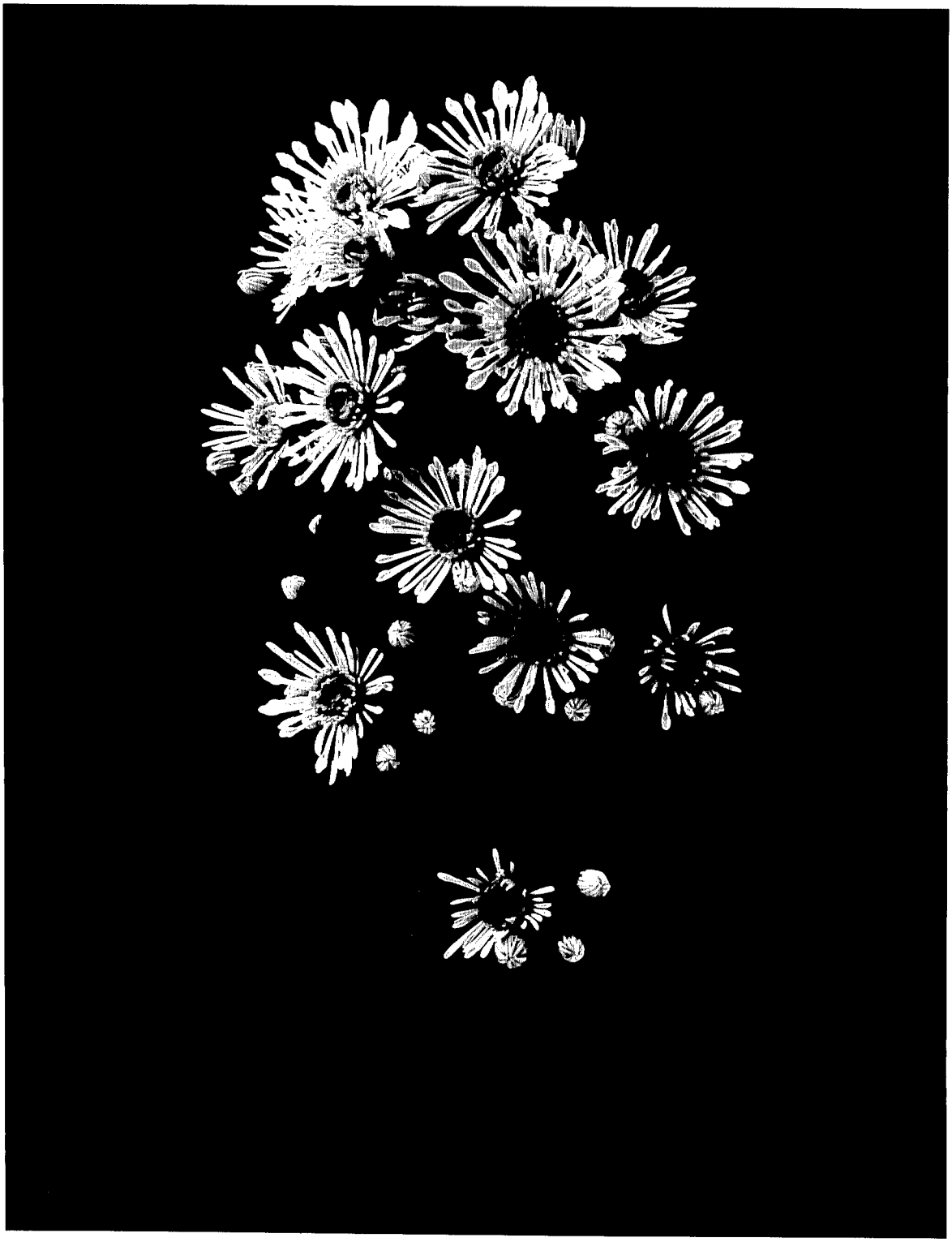

* * * * *